Figure 5:
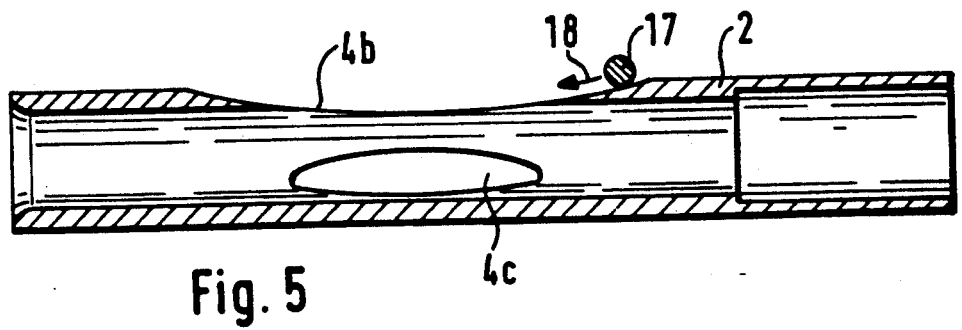

United States Patent [19]

Günther

[11] Patent Number: 5,020,537
[45] Date of Patent: Jun. 4, 1991

[54] MEASURING PROBE

[75] Inventor: Martin Günther, Wildberg, Fed. Rep. of Germany

[73] Assignee: Hewlett-Packard Company, Palo Alto, Calif.

[21] Appl. No.: 326,582

[22] Filed: Mar. 20, 1989

[30] Foreign Application Priority Data

Apr. 9, 1988 [EP] European Pat. Off. ........ 88105675.8

[51] Int. Cl.$^5$ .............................................. A61B 6/00
[52] U.S. Cl. .................................... 128/634; 128/665
[58] Field of Search ................. 128/633, 634, 635, 665

[56] References Cited

U.S. PATENT DOCUMENTS 3,674,013 7/1972 Polanyl ............................ 128/634
4,016,863 4/1977 Brantigan .

FOREIGN PATENT DOCUMENTS 0176865 9/1985 European Pat. Off. .
0255234 6/1987 European Pat. Off. .

Primary Examiner—William E. Kamm
Assistant Examiner—John C. Hanley

[57] ABSTRACT

A measuring probe for the invasive measurement of blood parameters such as pH, $pO_2$ or $pCO_2$ comprises one or more optical fibers in a tubing. These optical fibers end up in sensors which are surrounded by a sheath. An additional wire is guided both in the tubing and the sheath. At the proximal end of the probe, the wire is connected to locking means closing the sheath at its outer end, whereas, at the distal end thereof, the wire is fastened to the tubing or to a connector. Therefore, this wire ensures perfect strain relieving of the probe.

6 Claims, 4 Drawing Sheets

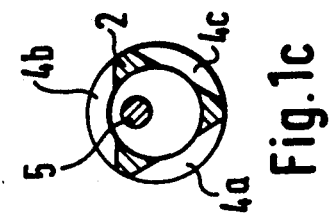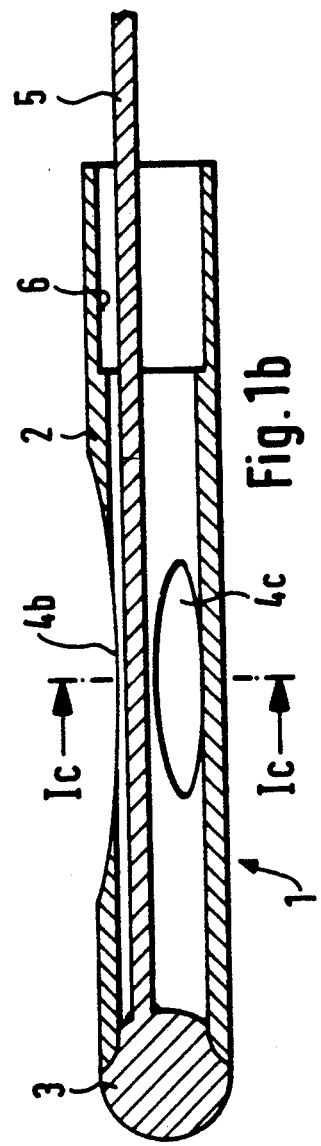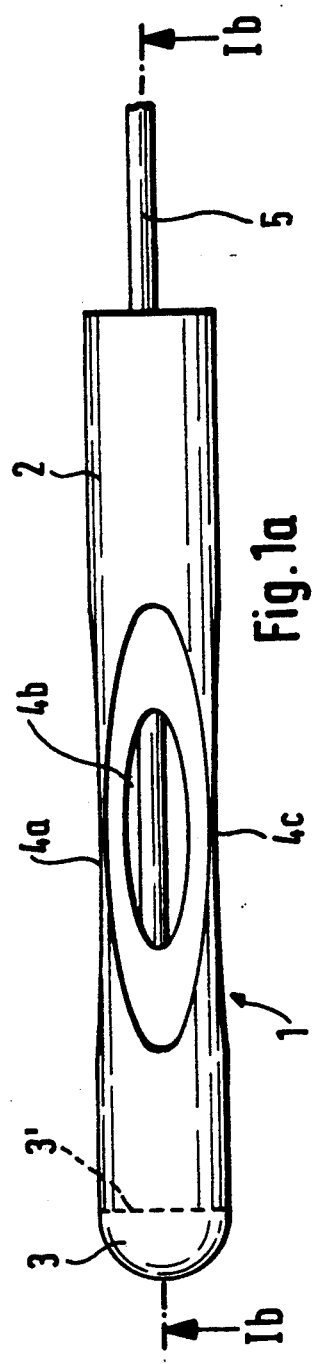

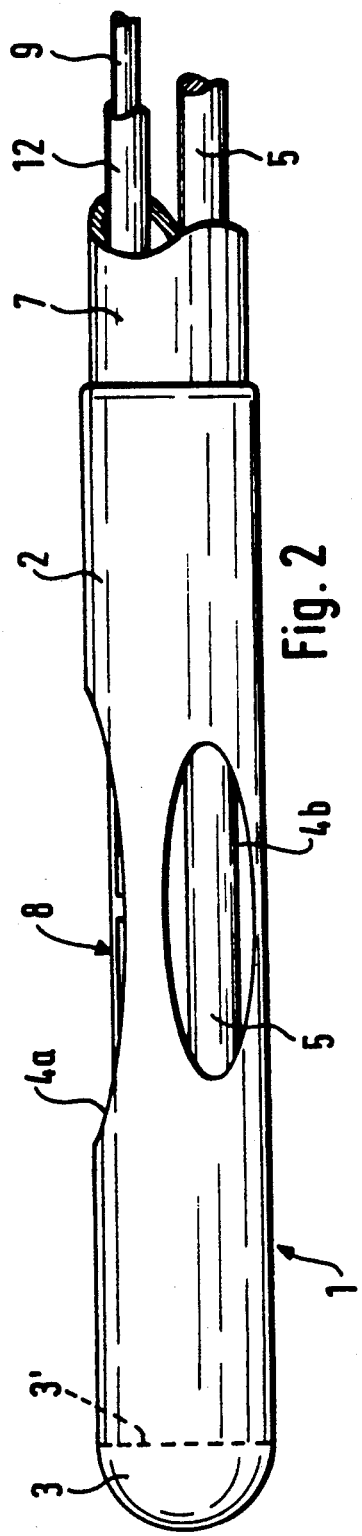
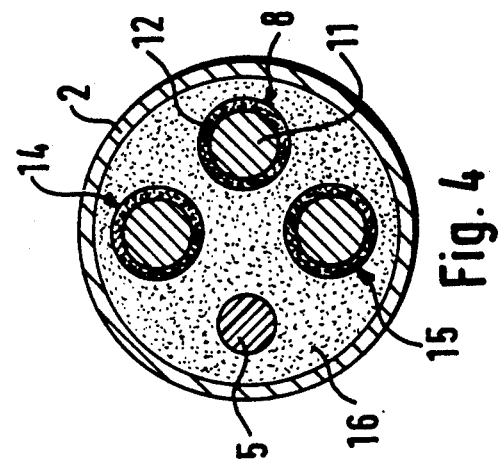
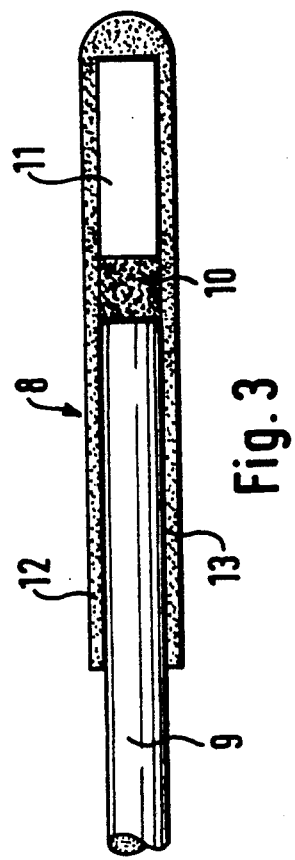

MEASURING PROBE

DESCRIPTION

This invention relates to a measuring probe for the invasive measurement of blood parameters such as pH, $pO_2$ or $pCO_2$ with at least one optical fiber guided in a tubing element and connected at its proximal end to a sensor which is surrounded by a tube-like sheath.

Probes for the invasive measurement of blood parameters consist of at least one sensor comprising an optical fiber, said fiber ending up with a gel zone containing a dye. The optical density or another optical parameter of said dye varies with the blood parameter (such as pH) to be measured. On the other side of the dye-containing gel, a reflector is positioned. The end of the fiber, the gel and the reflector are surrounded by a semi-permeable envelope (for example, a hydrogen ion permeable envelope in the case of a pH sensor) to keep the gel in place.

Light from this optical fiber passes the dye-containing gel, is reflected by said reflector, passes the gel again and is transmitted through the optical fiber to an appropriate detector which measures light attenuation or changes in other optical parameters caused by the dye. This attenuation or change is a function of the blood parameter to be measured, and the relation between attenuation, absorbance or the change of another optical parameter and the blood parameter is well-known.

Such a probe can be introduced in the patient's artery to measure —depending on the dye and/or the selected semi-permeable envelope—various blood parameters such as pH, $pO_2$ or $pCO_2$.

For further details of fiber optic pH measurement, reference is made to the essay "A Miniature Fiber Optic pH Sensor for Physiological Use" published in the Journal of Biomechanical Engineering, May 1980, pg. 141.

As the measuring probe is introduced into the artery, it is a major problem to guarantee absolute mechanical stability for the assembled probe. It has to be ensured that no part of the probe, in particular of the probe tip, can break off or be sheared off as such an incident could lead to embolism and, therefore, even to the death of the patient.

Up to now, the mechanical stability of such a probe is only guaranteed by the connection between the tubing element and the sheath covering the probe tip. With respect to stability, this is the most sensitive portion of the probe as tearing-off of the sheath would leave the same in the artery of the patient.

It is a major objective of the present invention to provide a measuring probe which guarantees complete mechanical stability and, in particular, a completely firm connection between the tubing element and the sheath.

According to the invention, this problem is solved for a measuring probe of the type described above by the following features:

(1.1) The sheath is closed at its outer end by locking means, (1.2) a wire is fastened to the inner side of said locking means, (1.3) said wire is guided in the tubing element and (1.4) said wire is fastened to a distal portion of the probe, preferably to said tubing element or to connecting means.

Such a probe comprises a wire which is—as well as the optical fiber(s) leading to the sensor(s) and in parallel to them—guided in the tubing element. The wire then passes the sheath (in parallel to the sensor(s)) and is fastened to the locking means (e.g., a metal cap) which closes the sheath at its outer end and is preferably connected with the same.

The wire is preferably carried to the outside through a hole in the tubing element and glued to the outer side of the tubing element by means of a plastic part. This is performed in a distal portion of the probe (in the terms of this description, "distal end" of the probe means those portions of the probe which are not to be introduced into the patient's body; "proximal end" means the end of the probe which is near the body of the patient, i.e. to be introduced into the patient's artery, and "outer end" of the sheath means its most proximal end).

Alternatively, the wire may also be fastened to a connector or the like; in this case, the optical fiber is also connected to said connecting means, said optical fiber providing light guidance from and to a monitor and the wire ensuring strain relieving of the probe.

Such a measuring probe ensures a very tight mechanical connection between all probe components. In particular, the sheath cannot get off the tube, and no break of the probe distal to the sensor tip can occur (measuring probes according to the state of the art could even break off in this region which is also partially introduced into the patient's artery). The strain relieving wire also ensures that no break of a sensor or an optical fiber can occur as all or at least most tension forces are absorbed by the wire parallel to the sensor(s)/optical fiber(s).

This is achieved by the basic idea of an additional wire guided in the tubing element in parallel to the optical fibers and fixed at both ends to the outer sheathing (the sheath at the proximal end and the tubing or the connector at the distal end). Neither the sheath, the tubing, the sensor(s) nor the optical fiber(s) have to absorb major tension forces, and, therefore, the new probe is absolutely save for medical applications. It is understood that the wire (and, of course, the other components of the probe) must meet the requirements for medical applications. For example, stainless steel may be wellsuited for this purpose. A selection of wires for medical applications can be found in "Fabricating Medical Components from Wire", by Terry L. Bartel, MD&DI, September 1987, pg. 66 ff. A preferred wire for the present application is the "MP35N" wire, cf. Tables I and II in that essay.

Preferably, the sheath and/or the locking means consist of metal, in particular stainless steel. Although this is not mandatory, it increases the mechanical stability of the probe tip; furthermore, metal is easy to sterilize, and the metal/metal connections (e.g., sheath to locking means and locking means to wire) may be welded or soldered. This is of particular importance for the connection between the wire and the locking means as the wire can only fulfill its strain relieving function if this connection is reliable. Still another solution may be selected, e.g. to embed the wire in a plastic locking means.

Advantageously, the locking means has a sphere-like contour. As it is important that the outer contour of the locking means fits well in a patient's artery without violating it, metal as the basic material for the locking means has the advantage that finishing can be performed after the attachment of the locking means to the sheath. Preferably, this finishing is performed by electropolishing which ensures that the outer contour of the locking means as well as its (welded or soldered) connection to the sheath is extremely smooth.

The invention further refers to a method for manufacturing a measuring probe of the type described above wherein the sheath as well as the locking means consist of metal. According to this method, the wire is first passed through said sheath, and then said locking means is welded or soldered to said sheath as well as to said wire in a single welding or soldering process. This method ensures that both relevant connections (locking means to sheath and wire to locking means) can be welded or soldered and is—due to the fact that only a single manufacturing step is necessary—very easy to perform. A very solid and smooth welding connection even in the small dimensions of such a measuring probe may be obtained if welding is performed by a laser, preferably in an argon atmosphere. As just mentioned, the outer side of the locking means and its connection to the sheath may be electropolished afterwards to remove any projecting burrs.

For the purpose of measuring blood parameters, the sheath must have openings or the like to allow ions or molecules to come into contact with the sensors. As just outlined above, it is evident that a patient's artery is not injured by the outer contour of the probe. Therefore, according to a further advantageous aspect of the invention, the edges of the window(s) of the sheath are rounded. It has turned out in a lot of tests that the best method to obtain such rounded edges is to use the spark erosion technique.

In the accompanying drawings, a preferred embodiment of the present invention is shown. More features and advantages are contained in the following description in which these drawings are explained.

Figure 6:
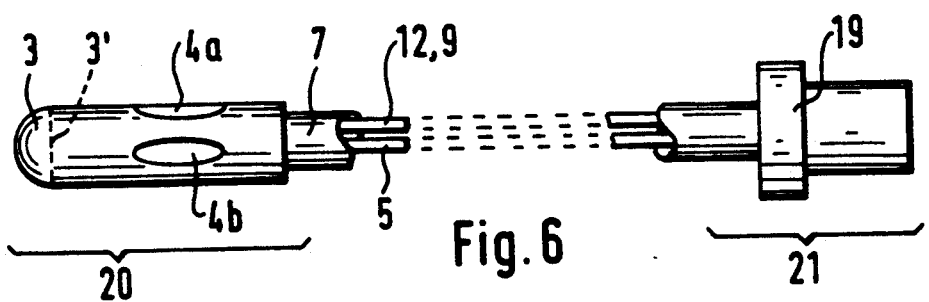
Figure 7:
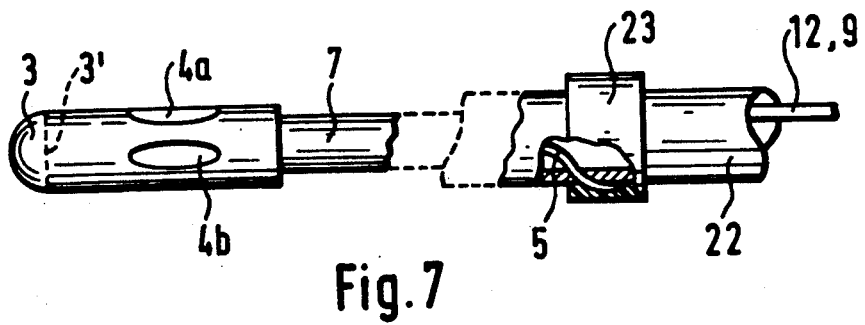
Figure 8:
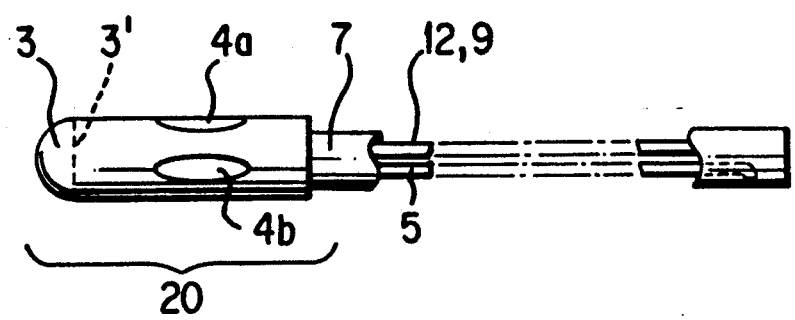
Figure 9:
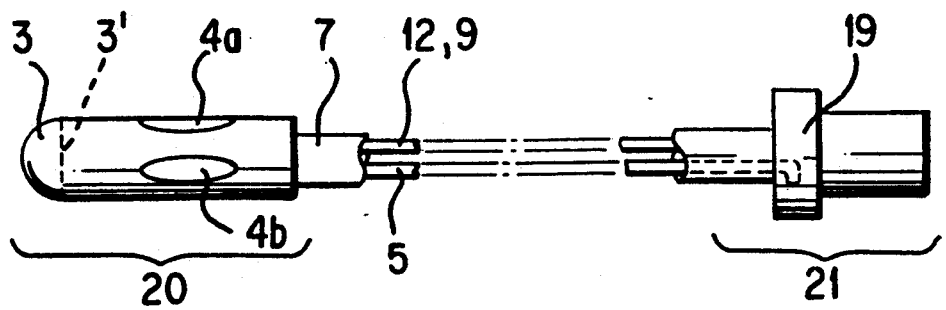

In the drawings,

FIG. 1a is a side view of the probe tip of a measuring probe according to the invention without tubing element and without sensors, FIG. 1b is a longitudinal section along line Ib—Ib of FIG. 1a, FIG. 1c is a cross section along line Ic—Ic of FIG. 1b, FIG. 2 is an outside view of the probe tip of an assembled measuring probe, FIG. 3 depicts a longitudinal section of a single sensor and its associated optical fiber, FIG. 4 is a cross section of the probe tip of an assembled measuring probe, FIG. 5 is a longitudinal section of the sheath illustrating the process of manufacturing its windows, FIG. 6 depicts a schematic diagram of a complete measuring probe, and FIG. 7 depicts a schematic diagram of another measuring probe showing attachment of a strain-relieving wire therein, FIG. 8 depicts a schematic diagram of a complete measuring probe showing attachment of a strain-relieving wire in an alternative embodiment, and FIG. 9 depicts a schematic diagram of a complete measuring probe showing attachment of a strain-relieving wire in a further alternative embodiment.

FIG. 1a depicts a probe tip 1 of a measuring probe for the invasive measurement of blood parameters. This probe tip is not yet completely assembled. A metal sheath 2, closed at its outer end by sphere-like locking means 3, is provided for introduction into a patient's artery. Sheath 2 further provides three windows 4a, 4b and 4c with inclined edges. A metal wire 5 is provided for strain relieving.

FIG. 1b—which is a cross section along line Ib—Ib of FIG. 1a—depicts the contour of sphere-like locking means 3. This locking means also consists of metal, in particular stainless steel. In the manufacturing process, wire 5 is first passed through sheath 2 (from the right to the left) and then welded in an argon atmosphere by a laser to locking means 3. Simultaneously, locking means 3 is welded to sheath 2 (same manufacturing process). Finally, the outer contour of locking means 3 is electropolished; in particular, burrs protruding at the connection line 3' between locking means 3 and sheath 2 are removed. Although indicated as 3', the connection line between locking means 3 and sheath 2 is no longer visible after electropolishing. Sheath 2, locking means 3 and wire 5 consist of the same material and form an integral part after welding or soldering. Locking means 3 may—as in the present example—also be formed from the material of wire 5 and sheath 2 upon welding or soldering.

Sheath 2 further defines a recess 6 for the introduction of a flexible tubing as will be explained below. Windows 4a to 4c allow the blood to reach the sensors as will be also explained below.

Wire 5 serves as a strain relieving member and is therefore not only attached to locking means 3 at the outer end of sheath 2, but also at its distal end to a connector or to the Kevlar fibers of the tubing (FIG. 8).

FIG. 1c depicts a cross section along line Ic—Ic of FIG. 1b. This cross section shows openings or windows 4a to 4c in detail.

FIG. 2 depicts an outside view of a completely assembled probe tip 1. Sheath 2 is connected (e.g. by an adhesive or glue) to a tubing 7. Sheath 2 contains wire 5 as well as three sensors one of which (8) is shown in FIG. 2 (with respect to the other sensors, see FIG. 4).

The details of a sensor shall now be discussed in detail with reference to FIG. 3. This figure depicts a longitudinal section through a sensor and the associated optical fiber. With reference to FIG. 2, the left and right side are reversed in FIG. 3.

Light guided in an optical fiber 9 reaches a dye-containing gel 10 in sensor 8. The absorption spectrum of dye 10 is dependent on the parameter to be measured. For a pH sensor, the dye may be phenol red.

The transmitted light is then reflected at reflector 11. Preferably, this reflector is made of metal such as platinum or stainless steel, the surface of this metal being polished on the side of gel 10. The reflected light passes dye-containing gel 10 again and is directed back through optical fiber 9 and appropriately received by and processed in a monitor. The whole system is packed in a selective membrane or envelope 12, this membrane being permeable for the ions or gas molecules to be measured—in case of a pH electrode, for hydrogen ions—, so that these ions/gas molecules can reach the dye-containing gel. Membrane 12 is fastened on optical fiber 9 and reflector 11 by a glue 13. The preferred material for membrane 12 is a hydrophilic material such as cellulose.

Now returning to FIG. 2, it is evident that windows 4a to 4c are required to allow ions or gas molecules to reach the selective membranes and, consequently, the dye-containing gel of the sensors.

FIG. 4 is a cross section of the measuring probe in the region of sheath 2 near its outer end, i.e. outside windows 4a to 4c. As just explained, this sheath contains wire 5 and a sensor 8 (e.g., a pH sensor) of which reflector 11 and envelope 12 can be seen in FIG. 4. Further sensors shown in FIG. 4 are a $pO_2$ sensor 14 and a $pCO_2$ sensor 15 which are basically equal to sensor 8 (but, of course, contain other dyes and/or envelopes depending on the parameter to be measured). The sheath itself is filled with a glue or adhesive 16 which holds the sensors and the wire in place.

FIG. 5 is a longitudinal section of sheath 2 and illustrates manufacturing of the rounded edges of window 4b. A wire 17 is moved in a direction perpendicular to its axis (cf. arrow 18) and thereby provides a window 4b with rounded edges. Dependent on the movement of wire 17, the edges of window 4b may be given any desired profile.

FIG. 6 depicts a schematical outside view of the complete measuring probe. Tubing 7 is partially broken away to show wire 5 and membrane 12 covering optical fiber 9. The other optical fibers are not shown in FIG. 6.

A connector 19 is provided for connection with a monitor which contains a light source and a light receiving means. All optical fibers and wire 5 are fastened to said connector, the optical fibers to ensure light guidance and wire 5 to ensure strain relieving of the measuring probe (FIG. 9).

Proximal end 20 of the measuring probe (the probe tip) is intended for introduction into a patient's artery, whereas the other end 21 is—as just mentioned—to be connected with a monitor.

FIG. 7 depicts another way of fastening the wire. The distal portion (which is not to be introduced into the patient's artery) of tubing 7 is thicker (indicated by reference number 22). In this portion, wire 5 runs through a hole in the tubing (see the broken-away region in FIG. 7) and is fixed to the outside by means of a glued plastic sleeve 23. This solution has—with reference to the embodiment of FIG. 6—the advantage that there is no danger of an unwanted electrical connection between the monitor and the probe.

I claim:
1. An optical probe comprising:
an outer sheath comprising a first end, a second end, and at least one opening therethrough between said first end and said second end, said first end being adapted for receipt within the artery of a patient and comprising a rigid spherical member;
a tubular conduit operatively connected to said sheath comprising an inner end positioned within said sheath, and an outer end extending beyond said second end of said sheath;
at least one sensor unit positioned within said tubular conduit comprising an optical fiber, a portion of gel having at least one dye therein, and a reflector unit positioned adjacent said portion of gel for reflecting light from said optical fiber which has passed through said portion of gel; and
a wire positioned within said tubular conduit adjacent said sensor unit having a first end and a second end, said first end of said wire being fixedly secured to said rigid spherical member, and said second end of said wire being fixedly secured to outer end of said conduit.

2. The probe of claim 1 wherein said opening in said sheath comprises a continuous peripheral edge which is upwardly sloped to form an inclined surface around said opening.

3. An optical probe comprising:
an outer sheath comprising a first end, a second end, and at least one opening therethrough between said first end and said second end, said first end being adapted for receipt within the artery of a patient and comprising a rigid spherical member;
a tubular conduit operatively connected to said sheath comprising an inner end positioned within said sheath, and an outer end extending beyond said second end of said sheath;
at least one sensor unit positioned within said tubular conduit comprising an optical fiber, a portion of gel having at least one dye therein, and a reflector unit positioned adjacent said portion of gel for reflecting light from said optical fiber which has passed through said portion of gel;
a connecting member operatively secured to said outer end of said conduit; and
a wire positioned within said tubular conduit adjacent said sensor unit having a first end and a second end, said first end of said wire being fixedly secured to said rigid spherical member, and said second end of said wire being fixedly secured to said connecting member.

4. The probe of claim 3 wherein said opening in said sheath comprises a continuous peripheral edge which is upwardly sloped to form an inclined surface around said opening.

5. An optical probe comprising:
an outer sheath comprising a first end, a second end, and at least one opening therethrough between said first end and said second end, said first end being adapted for receipt within the artery of a patient and comprising a rigid spherical member;
a tubular conduit operatively connected to said sheath comprising an inner end positioned within said sheath, and an outer end extending beyond said second end of said sheath, said outer end having a diameter greater than the diameter of said inner end, said outer end further comprising at least one orifice therethrough;
at least one sensor unit positioned within said tubular conduit comprising an optical fiber, a portion of gel having at least one dye therein, and a reflector unit positioned adjacent said portion of gel for reflecting light from said optical fiber which has passed through said portion of gel;
a wire positioned within said tubular conduit adjacent said sensor unit having a first end and a second end, said first end of said wire being fixedly secured to said rigid spherical member, and said second end of said wire passing through said orifice in said outer end of said conduit; and
a retaining member secured to said outer end of said tubular conduit, said retaining member being positioned over said orifice in said outer end of said conduit and against said second end of said wire in order to secure said second end of said wire between said retaining member and said outer end of said conduit.

6. The probe of claim 5 wherein said opening in said sheath comprises a continuous peripheral edge which is upwardly sloped to form an inclined surface around said opening.

* * * * *